(12) United States Patent
Naubereit

(10) Patent No.: US 12,239,386 B2
(45) Date of Patent: Mar. 4, 2025

(54) METHOD FOR DETERMINING A POSITION OF A LASER FOCUS OF A LASER BEAM OF AN EYE SURGICAL LASER, AS WELL AS TREATMENT APPARATUS

(71) Applicant: SCHWIND eye-tech-solutions GmbH, Kleinostheim (DE)

(72) Inventor: Pascal Naubereit, Aschaffenburg (DE)

(73) Assignee: SCHWIND EYE-TECH-SOLUTIONS GMBH, Kleinostheim (DE)

( * ) Notice: Subject to any disclaimer, the term of this patent is extended or adjusted under 35 U.S.C. 154(b) by 646 days.

(21) Appl. No.: 17/331,061

(22) Filed: May 26, 2021

(65) Prior Publication Data
US 2021/0369356 A1 Dec. 2, 2021

(30) Foreign Application Priority Data
May 27, 2020 (DE) ...................... 10 2020 114 212.9

(51) Int. Cl.
*A61B 34/20* (2016.01)
*A61F 9/008* (2006.01)

(52) U.S. Cl.
CPC .............. *A61B 34/20* (2016.02); *A61F 9/008* (2013.01); *A61B 2034/2057* (2016.02); *A61B 2034/2065* (2016.02)

(58) Field of Classification Search
CPC ............ A61B 34/20; A61B 2034/2057; A61B 2034/2065; A61F 9/008; A61F 2009/00846; A61F 9/00827
See application file for complete search history.

(56) References Cited

U.S. PATENT DOCUMENTS

| 5,225,862 | A | * | 7/1993 | Nagano | ................... | G03B 13/02 |
| | | | | | | 396/125 |
| 5,738,677 | A | * | 4/1998 | Colvard | ................. | G02B 6/241 |
| | | | | | | 606/4 |
| 2003/0111447 | A1 | * | 6/2003 | Corkum | ............. | B23K 26/0624 |
| | | | | | | 219/121.76 |

(Continued)

FOREIGN PATENT DOCUMENTS

AU  28572/97 A  9/1997

OTHER PUBLICATIONS

Notification of the First Office Action issued Sep. 27, 2023 in CN Appl. No1 202110586317.8.

(Continued)

*Primary Examiner* — Brian T Gedeon
*Assistant Examiner* — Rumaisa Rashid Baig
(74) *Attorney, Agent, or Firm* — MEDLER FERRO WOODHOUSE & MILLS PLLC

(57) ABSTRACT

A treatment apparatus, a computer program, and a computer-readable medium for carrying out a method for determining a position of a laser focus of a laser beam of an eye surgical laser of a treatment apparatus by a control device of the treatment apparatus, in which the laser beam of the treatment apparatus is emitted into or onto a human or animal eye and in which at least two Purkinje images of the laser beam on the eye are captured by an optical capturing device of the treatment apparatus, and in which the position of the laser focus in or on the eye is determined by the control device considering the captured Purkinje images and considering an opening angle of the laser beam.

10 Claims, 2 Drawing Sheets

(56) References Cited

U.S. PATENT DOCUMENTS

| | | | | |
|---|---|---|---|---|
| 2004/0066489 A1* | 4/2004 | Benedikt | ............... | A61B 3/107 |
| | | | | 351/212 |
| 2007/0032782 A1* | 2/2007 | Youssefi | ............... | A61B 3/113 |
| | | | | 606/5 |
| 2010/0324542 A1* | 12/2010 | Kurtz | ............... | A61F 9/00825 |
| | | | | 606/6 |
| 2011/0172649 A1* | 7/2011 | Schuele | ............... | A61F 9/008 |
| | | | | 606/4 |
| 2012/0069298 A1* | 3/2012 | Ng | ............... | A61B 3/18 |
| | | | | 351/205 |
| 2014/0104576 A1* | 4/2014 | Bor | ............... | A61B 3/10 |
| | | | | 351/215 |
| 2014/0263219 A1* | 9/2014 | Chen | ............... | A61F 2/91 |
| | | | | 219/121.72 |
| 2014/0268042 A1* | 9/2014 | Bor | ............... | A61B 3/1005 |
| | | | | 351/246 |
| 2017/0056243 A1 | 3/2017 | Schuele et al. | | |
| 2019/0099076 A1* | 4/2019 | Fujikado | ............... | A61B 3/10 |
| 2019/0195688 A1* | 6/2019 | Atabaki | ............... | G01J 3/44 |

OTHER PUBLICATIONS

Arba Mosquera, Samuel et al., "Centration axis in refractive surgery," 2015, vol. 2, No. 1, pp. 1-16.

* cited by examiner

METHOD FOR DETERMINING A POSITION OF A LASER FOCUS OF A LASER BEAM OF AN EYE SURGICAL LASER, AS WELL AS TREATMENT APPARATUS

The invention relates to a method for determining a position of a laser focus of a laser beam of an eye surgical laser of a treatment apparatus by means of a control device of the treatment apparatus. Further, the invention relates to a treatment apparatus, to a computer program as well as to a computer-readable medium.

Opacities and scars within the cornea, which can arise by inflammations, injuries or congenital diseases, impair the sight. In particular in case that these pathological and/or unnaturally altered areas of the cornea are located in the axis of vision of the eye, clear sight is considerably disturbed. Hereto, different laser methods by means of corresponding treatment apparatuses are given from the prior art, which can separate a volume body from the cornea and thus improve the sight for a patient. These laser methods are in particular an invasive intervention such that it is of particular advantage for the patient if the intervention is performed in a time as short as possible and to a particularly efficient extent. Therein, a volume body in particular for example is to only include the altered area of the cornea. Therefore, based on the prior art, it is particularly important to be able to perform an accurate position determination of the devices of the treatment apparatus, which are used in the intervention.

Therefore, it is the object of the present invention to provide a method, a treatment apparatus, a computer program and a computer-readable medium, by means of which a current position of a laser focus can be determined in improved manner.

This object is solved by a method, a treatment apparatus, a computer program as well as a computer-readable medium according to the independent claims. Advantageous forms of configuration with convenient developments of the invention are specified in the respective dependent claims, wherein advantageous configurations of the method are to be regarded as advantageous configurations of the treatment apparatus, of the computer program and of the computer-readable medium and vice versa.

A first aspect of the invention relates to a method for determining a position of a laser focus of a laser beam of an eye surgical laser of a treatment apparatus by means of a control device of the treatment apparatus, in which the laser beam of the treatment apparatus is emitted into or onto a human or animal eye and in which at least two Purkinje images of the laser beam on the eye are captured by means of an optical capturing device of the treatment apparatus, and in which the position of the laser focus in the eye is determined by means of the control device considering the captured Purkinje images and considering an opening angle of the laser beam.

Thereby, it is in particular allowed that the pose of the laser focus in the eye, for example in a cornea of the eye, can be directly determined. Therefore, the risk of an incorrectly positioned treatment can be minimized. In particular, it can for example be avoided that non-meeting partial incisions, for example in case of lenticular incisions or in case of laser phacoemulsification or laser capsulotomy. Further, an injury of the endothelium can be prevented. Furthermore, a poorly positioned femto flap or lenticule and a concomitant incorrect refraction in the eye after the treatment can be prevented for a patient.

Presently, the relative angle is in particular to be understood by opening angle of the laser beam, which forms opposing peripheral beams of the laser beam to each other.

Thus, the solution according to the invention in particular exploits that the position of the laser focus in the three-dimensional space of the material to be processed, in particular within the eye, for example the cornea or a lens of the eye, can be determined by the relative pose and shape/structure of the at least two Purkinje images to each other considering the opening angle of the laser beam.

Overall, a treatment of the eye can be performed more patient-friendly by the determination of the position of the laser focus, since the position of the laser focus can be reliably determined and thus the treatment can be reliably performed in a correct and predetermined position of the eye.

Therein, the method according to the invention can be performed with a single control device of the treatment apparatus or with multiple control devices of the treatment apparatus.

According to an advantageous form of configuration, a respective size of the at least two Purkinje images and a relative position of the at least two Purkinje images to each other are taken into account by means of the electronic computing device for determining the position of the laser focus. In particular, the position of the laser focus changes according to arrangement of the at least two Purkinje images to each other and the size of the Purkinje images, respectively. Based on the determination of the Purkinje images, in particular of the size and the position to each other, thus, the position of the laser focus can be reliably determined based on the law of refraction and the law of reflection. Thereby, a more reliable treatment can be realized in or on the eye of the patient by means of the treatment apparatus.

Further, it has proven advantageous if at least a first order Purkinje image and a second order Purkinje image, which are captured at a respective interface of the cornea, are captured for determining the laser focus. The Purkinje images are in particular reflections of the laser beam on the eye. The eye has multiple interfaces. In particular, the cornea has an anterior interface and a posterior interface. The first order Purkinje image in particular arises at the anterior interface of the cornea. The second order Purkinje image in particular arises at the posterior interface of the cornea. The first order Purkinje image and the second order Purkinje image can in particular be simply captured by means of the optical capturing device since corresponding reflections are already early visible with low resolution by means of the capturing device.

Further, it has proven advantageous if a third order Purkinje image and a fourth order Purkinje image, which are each captured at respective interfaces of a lens of the eye, are captured for determining the position of the laser focus. In particular, the lens of the eye has an anterior interface and a posterior interface. The third order Purkinje image in particular arises based on a reflection on the anterior interface of the lens. The fourth order Purkinje image in particular arises by the reflection on the posterior interface of the lens of the eye. In particular by a determination of the relative pose of the respective Purkinje images to each other, in particular of the first order, second order, third order and fourth order Purkinje images, as well as the size thereof, the position of the laser focus in the three-dimensional space of the eye can be reliably determined. Thus, a reliable treatment by means of the treatment apparatus is allowed.

Alternatively, or additionally, it is to be pointed out that any combinations of the first order, second order, third order and fourth order Purkinje images can also be used for determining the position of the laser focus. Preferably, four Purkinje images are captured, and the position of the laser focus is determined based on the respective size and based on a relative position to each other.

In a further advantageous form of configuration, a working beam reduced in energy with respect to a treatment beam as the laser beam is emitted into the eye as the laser beam for determining the position of the laser focus. The working beam is in particular a laser beam, which does not cause a damage of the eye and in particular is not perceived as uncomfortable for the patient. Thus, for example before the actual treatment with the treatment apparatus, the position of the laser focus in the eye can already be determined and possibly readjusted without an incision for example being already generated. Only after the focus has been determined, a treatment beam is emitted, which then in turn has the corresponding energy to for example separate a volume body from the eye. Thus, a more efficient treatment more comfortable for the patient can be realized by means of the treatment apparatus.

According to a further advantageous form of configuration, the position of the laser focus is determined in regular time intervals during a treatment. In other words, it is examined in regular time intervals where the laser focus is located at this point of time. For example, if the laser focus of the laser beam should have changed, thus, a corresponding tracking of the laser focus can be initiated such that the incision can be reliably generated in the treatment. Thereby, incorrectly positioned incisions can for example be prevented, whereby an improved treatment of the eye can be realized.

It is also advantageous if the control of the laser for a working beam as the laser beam and/or a treatment beam as the laser beam is effected such that the laser emits laser pulses in a wavelength range between 100 nanometers and 1400 nanometers, in particular between 700 nanometers and 1200 nanometers, at a respective pulse duration between one femtosecond and 20 nanoseconds, in particular between ten femtoseconds and ten picoseconds, and a repetition frequency of greater than one kilohertz, in particular between 100 kilohertz and ten megahertz.

In a further advantageous form of configuration, topographic and/or pachymetric and/or morphologic data of the eye, in particular of the cornea and/or of the lens, is taken into account for determining the position of the laser focus. In particular, this data can for example be determined already before a treatment. Based on this data, the treatment can then be reliably performed, and the position of the laser focus can be reliably determined.

A second aspect of the invention relates to a treatment apparatus with at least one eye surgical laser and with at least one control device for the laser or lasers, which is formed to perform the steps of the method according to the first aspect.

Preferably, the treatment apparatus is formed as a rotation scanner and for example comprises a beam deflection device hereto.

In an advantageous form of configuration of the treatment apparatus, the treatment apparatus comprises a storage device for at least temporary storage of at least one control dataset, wherein the control dataset or datasets include control data for positioning and/or laser focusing of individual laser pulses on or in the eye, and includes at least one beam deflection device for beam guidance and/or beam shaping and/or beam deflection and/or beam focusing of a laser beam of the laser. Therein, the mentioned control datasets are usually generated based on a measured topography and/or pachymetry and/or morphology of the cornea or lens to be treated of the pathologically and/or unnaturally altered area to be removed within the eye. Further, the treatment apparatus includes at least one optical capturing device, which is preferably formed as a camera, and which is formed for capturing at least two Purkinje images on the eye.

Therein, it can be provided that the treatment apparatus comprises a single storage device and a single control device. Alternatively, it can be provided that different storage devices and control devices are formed within the treatment apparatus to perform a corresponding control of the laser and determination of the position of the laser focus.

Further features and the advantages thereof can be taken from the descriptions of the first inventive aspect, wherein advantageous configurations of the first inventive aspect are to be regarded as advantageous configurations of the respectively other inventive aspect.

A third aspect relates to a computer program including instructions, which cause the treatment apparatus according to the second inventive aspect to execute the method steps according to the first inventive aspect. A fourth aspect of the invention relates to a computer-readable medium, on which the computer program according to the third inventive aspect is stored.

Further features and the advantages thereof can be taken from the descriptions of the first and second inventive aspects, wherein advantageous configurations of each inventive aspect are to be regarded as advantageous configurations of the respectively other inventive aspect.

Further features are apparent from the claims, the figures and the description of figures. The features and feature combinations mentioned above in the description as well as the features and feature combinations mentioned below in the description of figures and/or shown in the figures alone are usable not only in the respectively specified combination, but also in other combinations without departing from the scope of the invention. Thus, implementations are also to be considered as encompassed and disclosed by the invention, which are not explicitly shown in the figures and explained, but arise from and can be generated by separated feature combinations from the explained implementations. Implementations and feature combinations are also to be considered as disclosed, which thus do not comprise all of the features of an originally formulated independent claim. Moreover, implementations and feature combinations are to be considered as disclosed, in particular by the implementations set out above, which extend beyond or deviate from the feature combinations set out in the relations of the claims.

In the figures, identical or functionally identical elements are provided with the same reference characters.

Figure 1:
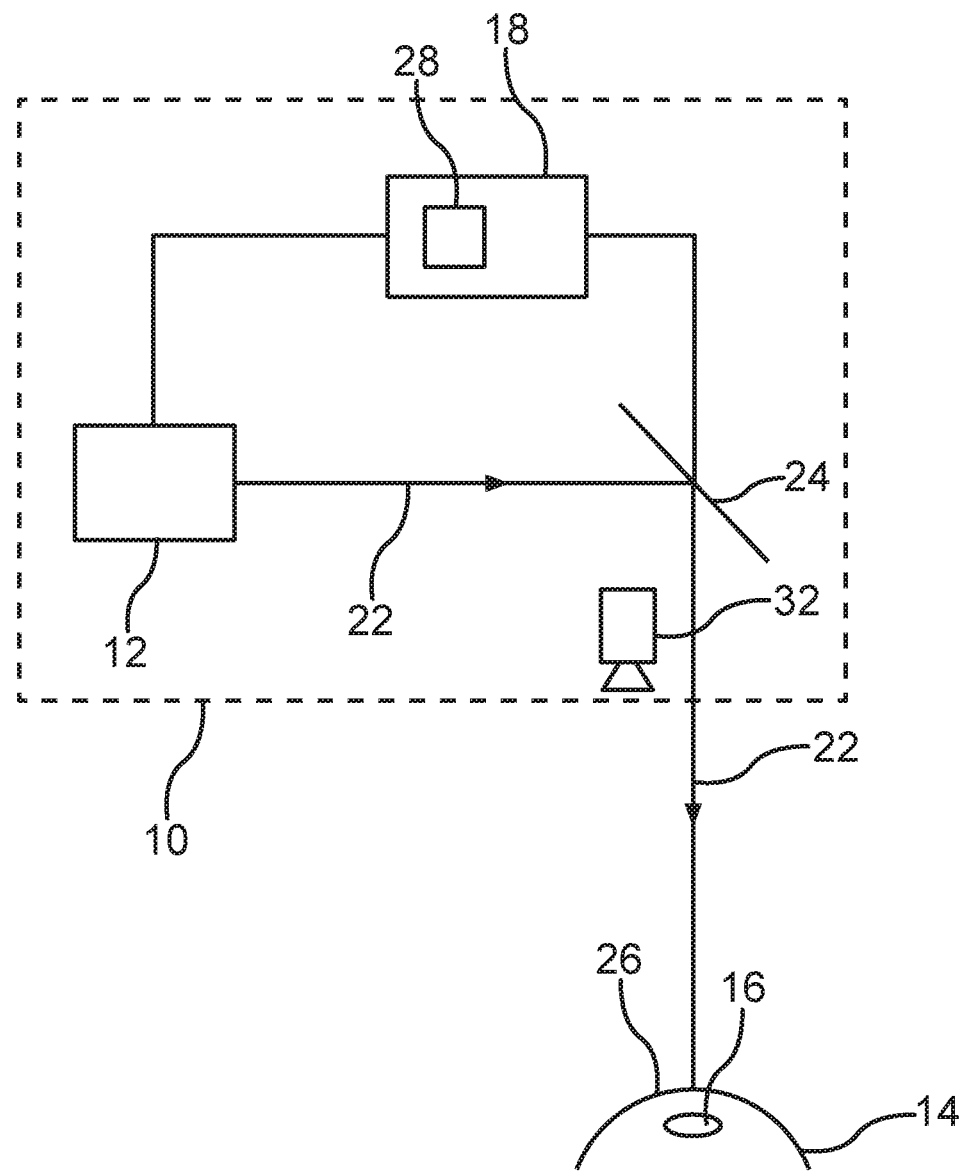
FIG. 1 shows a schematic representation of a treatment apparatus according to the invention.

FIG. 1 shows a schematic representation of a treatment apparatus 10 with an eye surgical laser 12 for the treatment of a patient, in particular for the treatment of an eye 14 of a patient. For example, a predefined corneal volume or cornea volume can be removed as a volume body 16 with predefined interfaces for example by means of photodisruption by means of the eye surgical laser 12. One recognizes that a control device 18 for the laser 12 is formed besides the laser 12. This form of configuration with a control device 18 is to be purely exemplarily regarded. It can be provided that the treatment apparatus 10 also comprises a plurality, in particular more than two, of control devices 18. The control device 18 can for example emit pulsed laser pulses in a predefined pattern into a cornea 20 (FIG. 2), wherein the interfaces of the volume body 16 to be separated are generated by the predefined pattern for example by means of photodisruption. In the illustrated embodiment, the interfaces of the volume body 16 form a lenticular volume body 16, wherein the position of the volume body 16 is selected in this embodiment such that a pathological and/or unnaturally altered area within a stroma of the cornea 20 is enclosed.

Furthermore, one recognizes that the laser beam 22 generated by the laser 12 is deflected towards a surface 26 of the eye 14 by means of a beam deflection device 24, such as for example a scanner, in particular a so-called rotation scanner. The beam deflection device 24 is also controlled by the control device 18 to for example generate the mentioned predefined pattern in the cornea 20. For example, the beam deflection device 24 can comprise one or also two mirrors, which are formed for deflecting the impinging laser beam 22.

In the present embodiment, the illustrated laser 12 is a so-called photodisruptive laser. Presently, the laser 12 is in particular formed to emit laser pulses in a wavelength range between 100 nanometers and 1400 nanometers, in particular between 700 nanometers and 1200 nanometers, at a respective pulse duration between one femtosecond and 20 nanoseconds, in particular between ten femtoseconds and ten picoseconds, and a repetition frequency of greater than one kilohertz, in particular between 100 kilohertz and 100 megahertz. Alternatively, the laser 12 can also be formed as an ablation laser. Further, the laser beam 22 can be generated both as a working beam with a lower energy than a treatment beam and as a treatment beam itself In addition, the control device 18 comprises a storage device 28 for at least temporary storage of at least one control dataset, wherein the control dataset or datasets include control data for positioning and/or for focusing individual laser pulses in or on the eye 14. The position data and/or focusing data of the individual laser pulses are generated based on a previously measured topography and/or pachymetry and/or the morphology of the eye 14 and the pathological and/or unnaturally altered area for example to be removed within the stroma of the eye 14.

Figure 2:
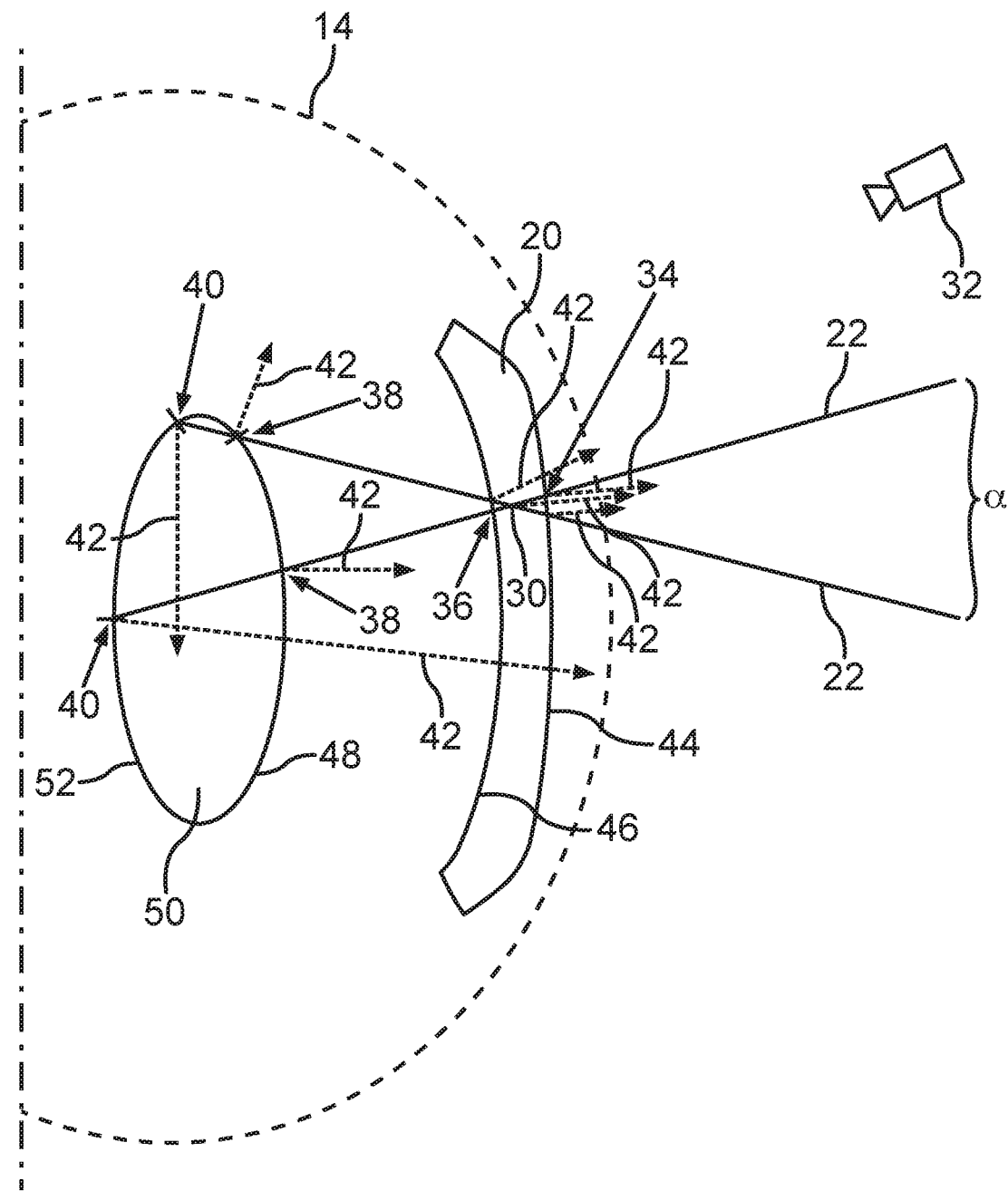
FIG. 2 shows a schematic side view of an eye of a patient.

FIG. 2 shows an eye 14 with the laser beam 22 in a purely schematic side view. Presently, the corresponding peripheral beams respectively opposing each other are in particular shown of the laser beam 22. The laser beam 22 has a laser focus 30, the position of which is presently formed in the cornea 20. An incision or a cavitation bubble for generating the volume body 16 is generated in the area of the laser focus 30. Thus, it is of crucial importance to reliably determine the position of the laser focus 30.

In the method for determining the position of the laser focus 30 of the laser beam 22 of the eye surgical laser 12 of the treatment apparatus 10 by means of the control device 18, the laser beam 22 of the treatment apparatus 10 is emitted onto or into the human or animal eye 14 and at least two Purkinje images 34, 36, 38, 40 of the laser beam 22 on the eye 14 are captured by means of an optical capturing device 32, in particular by means of a camera, of the treatment apparatus 10, and the position of the laser focus 30 in the eye 14, in particular in the cornea 20, is determined by means of the control device 18 considering the captured Purkinje images 34, 36, 38, 40 and considering an opening angle α, which is represented by means of the peripheral beams, of the laser beam 22.

Presently, a first order first Purkinje image 34 is shown. The first Purkinje image 34 is in particular generated by reflection, which is shown by the arrows 42, on an anterior interface 44 of the cornea 20. A second Purkinje image 36 is in particular a second order Purkinje reflection. The second Purkinje image 36 is generated at a posterior interface 46 of the cornea 20. A third Purkinje image 38 is in particular a third order reflection, wherein this reflection is in particular generated at an anterior interface 48 of a lens 50 of the eye 40. A fourth Purkinje image 40 is in particular a fourth order Purkinje reflection, which is in particular generated at a posterior interface 52 of the lens 50. In the present embodiment, the fourth Purkinje image 40 is in particular not completely reflected. As presently shown, the boundaries of the Purkinje images 34, 36, 38, 40 arise based on the respective peripheral beams of the laser beam 22.

For determining the position of the laser focus 30, it is in particular provided that a respective size of the at least two Purkinje images 34, 36, 38, 40 and a relative position of the at least two Purkinje images 34, 36, 38, 40 to each other are taken into account by means of the control device 18 for determining the position of the laser focus 30. Preferably, it can be provided that at least the first Purkinje image 34 and the second Purkinje image 36 are captured at the respective interfaces 44, 46 of the cornea 20 to determine the position of the laser focus 30. Additionally, or instead, the third Purkinje image 38 or the fourth Purkinje image 40 of the lens 50 can also be captured to contribute to the determination of the position of the laser focus 30. Any combinations of the Purkinje images 34, 36, 38, 40 are possible for determining the position of the laser focus 30. Preferably, the four Purkinje images 34, 36, 38, 40 are for example captured and the position of the laser focus 30 is determined depending thereon.

Further, it can for example be provided that a working beam reduced in energy with respect to a treatment beam as the laser beam 22 during a treatment is emitted to the eye 14 as the laser beam 22 for determining the position of the laser focus 30. Thereby, it is in particular allowed that generation of for example cavitation bubbles does not yet occur in the determination of the position of the laser focus 30, whereby a treatment itself is not yet performed in the determination of the position of the laser focus 30, but only the position of the laser focus 30 is determined without invasive intervention. For example, the energy of the working beam can be below the minimum energy for generating a cavitation bubble. Further, it can be provided that the determination of the position of the laser focus 30 is performed in regular time intervals during a treatment. In particular, it can for example be provided that a working beam reduced in energy is emitted in prescribed time intervals during the treatment to determine the position of the laser focus 30. In other words, it is changed between the treatment beam and the working beam with a lower energy such that the position of the laser focus 30 can be determined during the treatment itself Further, it is in particular provided that topographic and/or pachymetric and/or morphologic data of the eye 14, in particular of the cornea 20 and/or of the lens 50, is taken into account for determining the position of the laser focus 30.

For determining the position of the laser focus 30, it can in particular be provided that the control device 18 determines the position of the laser focus 30 based on the law of refraction and the law of reflection as well as based on the Purkinje images 34, 36, 38, 40 and considering the opening angle α. Thereby, it is allowed that the position of the laser focus 30 in the material, in particular within the cornea 20 and/or the lens 50, can be directly determined. Thereby, the risk of an incorrectly positioned treatment can for example be minimized. In particular, non-meeting partial incisions can for example be prevented from being generated. For example, in case of lenticule incisions or in case of laser phacoemulsification or laser capsulotomy, partial incisions can be prevented from not meeting. Further, an injury of the endothelium can be prevented. An incorrect refraction by an incorrectly positioned femto flap or the volume body 16 can also be prevented.

Thus, by the relative pose and the shape/structure of the Purkinje images 34, 36, 38, 40 to each other, or also further reflections on the eye 14, and considering the opening angle α, the position of the laser focus 30 can in particular be determined, the pose of which is located in the three-dimensional space of the material to be processed, for example in the cornea 20 or the lens 50.

Overall, the Figs. show a determination of the position of the laser focus 30 based on Purkinje images 34, 36, 38, 40.

What is claimed is:

1. A method for determining a position of a laser focus of a laser beam of an eye surgical laser of a treatment apparatus by a control device of the treatment apparatus, comprising:
    emitting into or onto a human or animal eye the laser beam of the treatment apparatus;
    capturing by an optical capturing device of the treatment apparatus at least two Purkinje images of the laser beam on the eye; and
    determining by the control device, in regular time intervals during a treatment, the position of the laser focus of the laser beam in or on the human or animal eye based on a respective size of the at least two Purkinje images, a relative position of the at least two Purkinje images to each other, and an opening angle of the laser beam.

2. The method according to claim 1, wherein at least a first order first Purkinje image and a second order second Purkinje, which are captured at a respective interface of a cornea of the eye, are captured for determining the position of the laser focus.

3. The method according to claim 1, wherein a third order third Purkinje image and/or a fourth order fourth Purkinje image, which are each captured at respective interfaces of a lens of the eye, are captured for determining the position of the laser focus.

4. The method according to claim 1, wherein the control of the laser for a working beam as the laser beam and/or a treatment beam as the laser beam is effected such that the laser emits laser pulses in a wavelength range between 100 nm and 1400 nm at a respective pulse duration between 1 fs and 20 ns and a repetition frequency of greater than 1 kHz.

5. The method according to claim 1, wherein topographic and/or pachymetric and/or morphologic data of a cornea of the eye and/or of a lens of the eye is taken into account for determining the position of the laser focus.

6. The method according to claim 1, wherein the at least two Purkinje images are captured by a capturing device comprising a camera.

7. A treatment apparatus with at least one eye surgical laser and with at least one control device for the laser or lasers, which is formed to perform the steps of the method according to claim 1.

8. The treatment apparatus according to claim 7, wherein the control device
    comprises at least one storage device for at least temporary storage of at least one control dataset, wherein the control dataset or datasets include control data for positioning and/or for focusing a laser beam into the eye;
    includes at least one beam device for beam guidance and/or beam shaping and/or beam deflection and/or beam focusing of a laser beam of the laser; and
    includes at least one optical capturing device for capturing at least two Purkinje images on the eye.

9. A non-transitory computer-readable medium having a computer program stored thereon, the computer program including instructions which cause a treatment apparatus with at least one eye surgical laser and with at least one control device for the at least one eye surgical laser to execute the method steps according to claim 1.

10. The method according to claim 4, wherein the wavelength range is between 700 nm and 1200 nm at the respective pulse duration of between 10 fs and 10 ps, and the repetition frequency of between 100 kHz and 10 MHz.

* * * * *